USOO5743887A

United States Patent [19]
Brattesani

[11] Patent Number: 5,743,887
[45] Date of Patent: Apr. 28, 1998

[54] SYRINGE SAFETY SLEEVE ADAPTER APPARATUS

[76] Inventor: Steven J. Brattesani, 2561 Chestnut St., San Francisco, Calif. 94123

[21] Appl. No.: 683,058

[22] Filed: Jul. 16, 1996

[51] Int. Cl.⁶ ................................... A61M 5/00
[52] U.S. Cl. ................................. 604/192
[58] Field of Search .................. 604/197, 198, 604/263, 192, 110, 164, 165, 187, 180, 27, 38

[56] References Cited

U.S. PATENT DOCUMENTS

| | | |
|---|---|---|
| 3,890,971 | 6/1975 | Leeson et al. |
| 4,631,057 | 12/1986 | Mitchell |
| 4,747,837 | 5/1988 | Hauck |
| 4,790,827 | 12/1988 | Haber et al. |
| 4,826,491 | 5/1989 | Schramm |
| 4,832,696 | 5/1989 | Luther et al. |
| 5,057,079 | 10/1991 | Tiemann et al. |
| 5,591,138 | 1/1997 | Vaillancourt ............. 606/192 |

FOREIGN PATENT DOCUMENTS

| | | |
|---|---|---|
| 96637 | 8/1960 | Norway. |
| 1191634 | 5/1970 | United Kingdom. |
| 2209946 | 6/1989 | United Kingdom. |

*Primary Examiner*—Michael Buiz
*Assistant Examiner*—William Lewis
*Attorney, Agent, or Firm*—John P. O'Banion

[57] ABSTRACT

A syringe safety sleeve apparatus having a hollow inner barrel which couples to a conventional syringe device, and a hollow outer sleeve slidably disposed on the inner barrel. The outer sleeve reversibly slides on the inner barrel between a retracted position and an extended, needle covering position to protect users of the invention from the syringe needle. A docking base is included which provides for protecting persons from needle puncture wounds during attachment and removal of needles from the syringe device, during removal and replacement of needle covers on needles, and during disposal of used needles.

17 Claims, 11 Drawing Sheets

SYRINGE SAFETY SLEEVE ADAPTER APPARATUS

BACKGROUND OF THE INVENTION

1. Field of the Invention

The invention pertains generally to syringes and devices for injecting or withdrawing liquid substances via needles, and more particularly to a safety sleeve apparatus which is reversibly attachable to syringes, which provides a slidably extending shield or sheath that protects persons from syringe needles during all stages of use and disposal.

2. Description of the Background Art

The increasing incidence of dangerous infectious diseases such as HIV, hepatitis B and like afflictions has lead to increasing safety concerns in the handling and use of syringes and needles. Syringe needles which are used to administer drugs to a patient or to withdraw blood or other bodily fluid from a patient become potentially contaminated and pose a risk to persons who handle the syringes and subsequently remove, dispose of or otherwise handle the needles and may inadvertently experience a puncture wound from a contaminated needle.

Various devices and methods have been developed to protect persons from used or contaminated syringe needles. Replaceable needle covers have been long known, but pose a risk to persons attempting to replace the covers onto used needles. The use of movable protective sheaths on disposable syringe devices is also known. Background art needle sheath devices generally comprise a part of a disposable syringe device, with the sheath manually extended to a permanently locked position to encase and protect the syringe needle after use and disposal.

An important drawback in known needle protecting devices is that they are generally single-use devices provided together with disposable syringes, and cannot be used with non-disposable syringes such as the autoclavable aspirating syringes and intraligamental syringes commonly used in the dental and medical professions for administering anesthetics and other drugs. Currently, no protective sheath devices are available for use with such non-disposable syringes. Further, background art needle protecting devices generally lock permanently in an extended, needle covering position, and thus cannot be used to protect persons from exposed needles prior to use. Additionally, since currently known needle protecting devices permanently lock over the needle after use, there is no provision for protecting persons during removal of contaminated needles from non-disposable syringes.

Accordingly, there is a need for a syringe safety sleeve adapter apparatus which can be interchangeably used with different non-disposable syringes, which provides for reversible sheathing or enclosure of an exposed needle, and which protects persons from syringe needles at every stage of use, including prior to injection and during removal of used needles. The present invention satisfies these needs, as well as others, and generally overcomes the deficiencies found in the background art.

SUMMARY OF THE INVENTION

The present invention is a syringe safety sleeve adapter apparatus which is suitable for interchangeable use with conventional non-disposable aspirating syringes, intraligamental syringes and other non-disposable syringe devices. In its most general terms, the invention comprises a cylindrical, hollow barrel, an outer cylindrical sleeve slidably and rotatably disposed on the barrel, means for reversibly locking the outer sleeve in an extended position, and means for coupling the cylindrical barrel to a syringe device. Preferably, a docking base is included with the invention for providing protection during removal of needle covers prior to using syringes, and for providing protection while replacing the needle cover on used needles and disposing of the used needles.

By way of example and not of limitation, the hollow inner barrel of the invention generally fits over the syringe barrel of the syringe device. In a first embodiment of the invention, the hollow inner barrel couples to the syringe device by frictionally engaging the syringe barrel. In an alternative embodiment, the hollow inner barrel threadably couples to the syringe device in place of the syringe barrel. The hollow inner barrel of the invention may detachably couple to the syringe device by various threading, snap fitting, bayonet mounting, or other standard means. The locking means preferably comprises one or more laterally extending slots in the outer sleeve which reversibly engage one or more studs in a locking arrangement. A longitudinal slot or opening is provided in both the inner barrel and outer sleeve to allow loading of anesthetic or other drug ampules into the syringe device both while the outer sleeve is in an extended needle covering position or in a retracted position. The docking base is provided with the invention for removal of needle covers from needles after the needles are attached to the syringe, and for replacement of needle covers and removal of the covered, contaminated needles after use. The docking base includes an opening structured and configured to receive the outer sleeve of the apparatus and means, associated with an internal bore, for reversibly holding a needle cover while a needle is removed from and replaced into the cover. The holding means preferably comprises a spring loaded rod which tensionally engages the needle cover, allowing the needle, while attached to the syringe device, to be disengaged from the cover prior to use and re-inserted in the needle cover after use. A trap door or opening in the bottom of the docking base allows covered, used needles to be disposed of from the docking base without handling of the used needles. The syringe safety sleeve adapter apparatus comprising the present invention is preferably made of autoclavable parts so that the invention may be heat sterilized and reused.

The invention is utilized by sliding the hollow, cylindrical inner barrel of the apparatus over the syringe barrel of a conventional syringe device, or, in the alternative embodiment attaching the inner barrel to the syringe device in place of the syringe barrel. While the outer sleeve of the apparatus is in a retracted position, a covered needle is attached to the syringe in a conventional manner. The covered needle is inserted into the bore of the docking base and the syringe safety sleeve adapter apparatus placed in the opening. The spring loaded rod engages and holds the needle cover while the cover is removed. As the uncovered needle is withdrawn from the bore in the docking base, the outer sleeve is slidably extended to enclose or protect the needle and is locked into the extended or needle-covering position. While the needle is used, the outer sleeve is unlocked and slidably retracted to allow insertion of the needle into patients. After use, the outer sleeve is extended again to cover or enclose the used needle. The end of the outer sleeve is then fitted into the opening of the docking base, and the outer sleeve is retracted, allowing the used needle to enter the bore in the docking base and insert back into the original needle cover held therein. The needle cover is then replaced on the used needle and the covered used needle is removed from the syringe while within the bore of the docking base. The spring loaded rod is disengaged from the needle cover, and the trap door in the bottom of the docking base is opened to allow disposal of the used needle through the bottom of the docking base and into an appropriate biohazardous waste receptacle. The syringe safety sleeve adapter apparatus of the invention is then removed from the syringe device and autoclaved or otherwise sterilized for reuse. The invention thus provides for protection from the syringe needle during every stage of use and eliminates the risk of inadvertent puncture wounds which may lead to transmission of infectious diseases. An object of the invention is to provide a syringe safety sleeve adapter apparatus which eliminates the risk of puncture wounds by contaminated needles which may cause transmission of infectious diseases.

Another object of the invention is to provide a syringe safety sleeve adapter apparatus which is usable with non-disposable syringe devices.

Another object of the invention is to provide a syringe safety sleeve adapter apparatus wherein a protective sleeve reversibly moves between a retracted position and an extended needle-protecting position.

Another object of the invention is to provide a syringe safety sleeve adapter apparatus which protects persons from exposed needles at every stage of syringe use, including the attachment and removal of needles and needle covers.

Another object of the invention is to provide a syringe safety sleeve adapter apparatus which can be interchangeably used with different syringe devices.

Another object of the invention is to provide a syringe safety sleeve adapter apparatus which is heat sterilizable and reusable.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Referring more specifically to the drawings, for illustrative purposes the present invention is embodied in the apparatus generally shown in FIG. 1 through FIG. 15. It will be appreciated that the apparatus may vary as to configuration and as to details of the parts without departing from the basic concepts as disclosed herein. The invention is disclosed generally in terms of use with a conventional aspirating syringe. However, the invention may be used with a variety of different types of syringe devices, as will be readily apparent to those skilled in the art.

Referring now to FIG. 1 through FIG. 10, a syringe safety sleeve apparatus 10 is generally shown. The apparatus 10 is shown in an embodiment which is structured and configured for use with a conventional aspirating syringe 12 of the type commonly used in the dental and medical professions for injection of patients with anesthetics and other drugs. The aspirating syringe device 12 generally includes a syringe barrel 14 which is detachably coupled to a base or handle 16, and a piston or plunger 18 which is slidably disposed within barrel 14 and base 16. A ring 20 and grips 22a, 22b are provided on syringe device 12 to facilitate hand actuation of plunger 18 in a conventional manner. A longitudinal, side-facing opening 24 is included in syringe barrel 14 to allow insertion of an anesthetic or other drug ampule (not shown). A pointed tip 26 on plunger 18 is provided for penetrating the ampule. Syringe barrel 14 includes needle attachment means at a first end 28, and a hip or widened portion 30 at a second end 32, with hip 30 having a slightly greater diameter or being otherwise thicker than the remainder of barrel 14. The needle attachment means typically comprises a needle adapter 34 which threadably engages opening 36 in first end 30 of barrel 14. A conventional syringe needle 38 includes a base 40 which detachably couples to ferrule 42 on needle adapter 34 by threading or friction. Needle 38 comes with a detachable cover 44 which encases and protects needle 38 and detachably engages needle base 40 by friction, threading, snap fitting, or the like. As mentioned above, syringe device 12 represents merely one type of syringe device which may be used with the invention, and the invention may be varied in structure and configuration to accommodate various types of syringe devices. The invention may be used with pistol-type intraligamental syringes, disposable syringes, and other commonly used syringe devices.

The syringe safety sleeve apparatus 10 generally comprises a sheath portion 46 which detachably couples to syringe device 12 to cover and protect persons from needles on syringe device 12, and a docking base 48 used with the sheath 46 for protecting persons from needles during attachment and removal of needles from syringe device 12. Sheath 46 includes an inner barrel 50 and an outer sleeve 52 which is slidably disposed on inner barrel 50. Inner barrel 50 is preferably of elongated, hollow, cylindrical structure and configuration, and includes a first end 54 and a second end 56, with an opening 58 at first end and an opening 60 at second end 56 such that a longitudinal bore 62 is defined along the length of inner barrel 50. Bore 62 is structured and configured to reversibly engage syringe barrel 14, as discussed further below. An elongated side-facing opening 64 in the side of inner barrel 50 communicates with bore 62.

Outer sleeve 52 is also of elongated, hollow, cylindrical structure and configuration, and has a radius or diameter which is slightly greater than that of inner barrel 50 so that outer sleeve 52 slidably fits over inner barrel 50 and can undergo longitudinal sliding motion and lateral sliding rotation thereon. Outer sleeve 52 includes first and second ends 66, 68, with an opening 70 provided at first end 66 and an opening 72 at second end 68. An elongated side-facing opening 74 in the side of outer sleeve 52 extends generally between first and second ends 66, 68.

Figure 1:
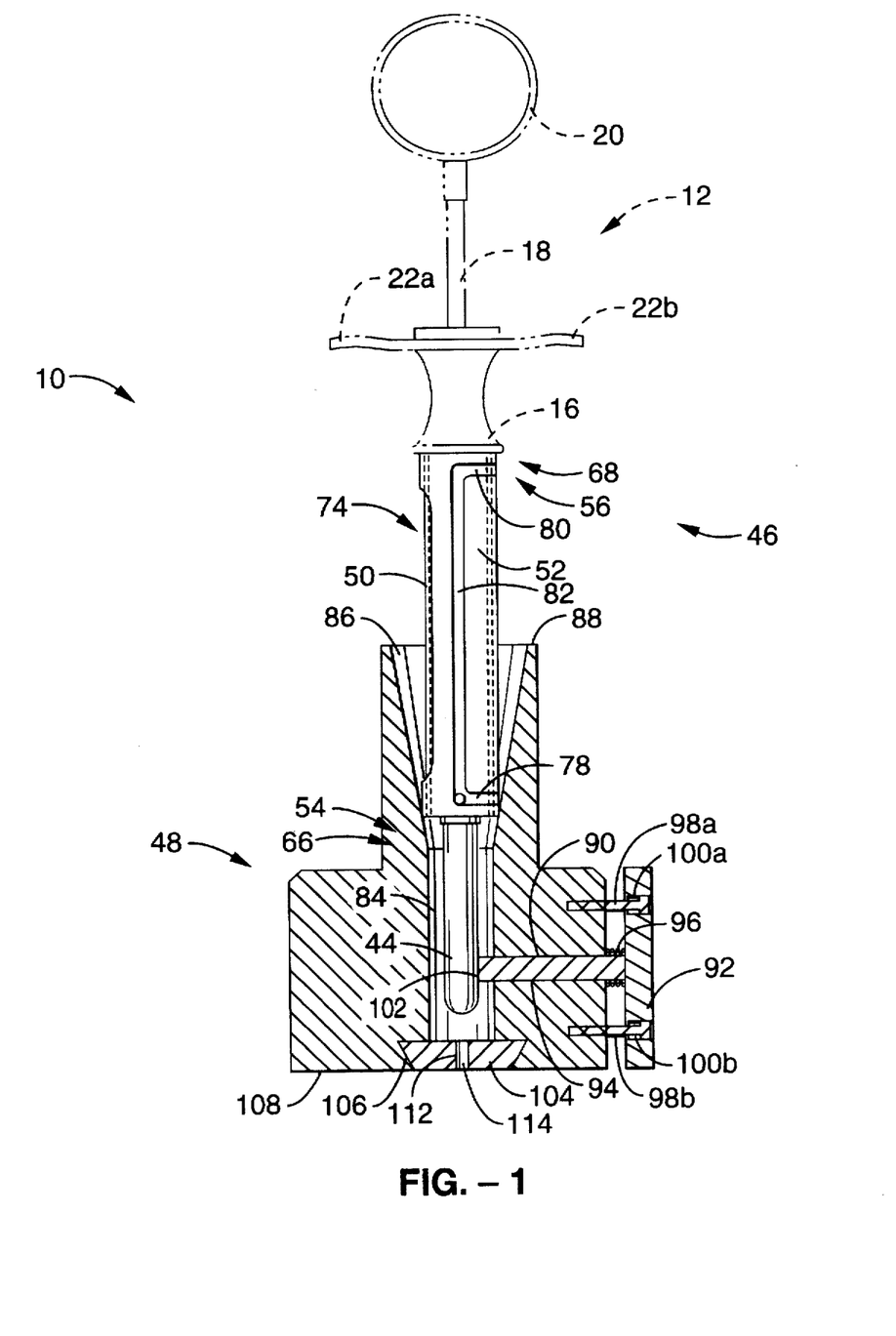
FIG. 1 is a side elevation view in cross-section of the syringe safety sleeve sheath and syringe apparatus of FIG. 1 engaged in a docking base.
Figure 2:
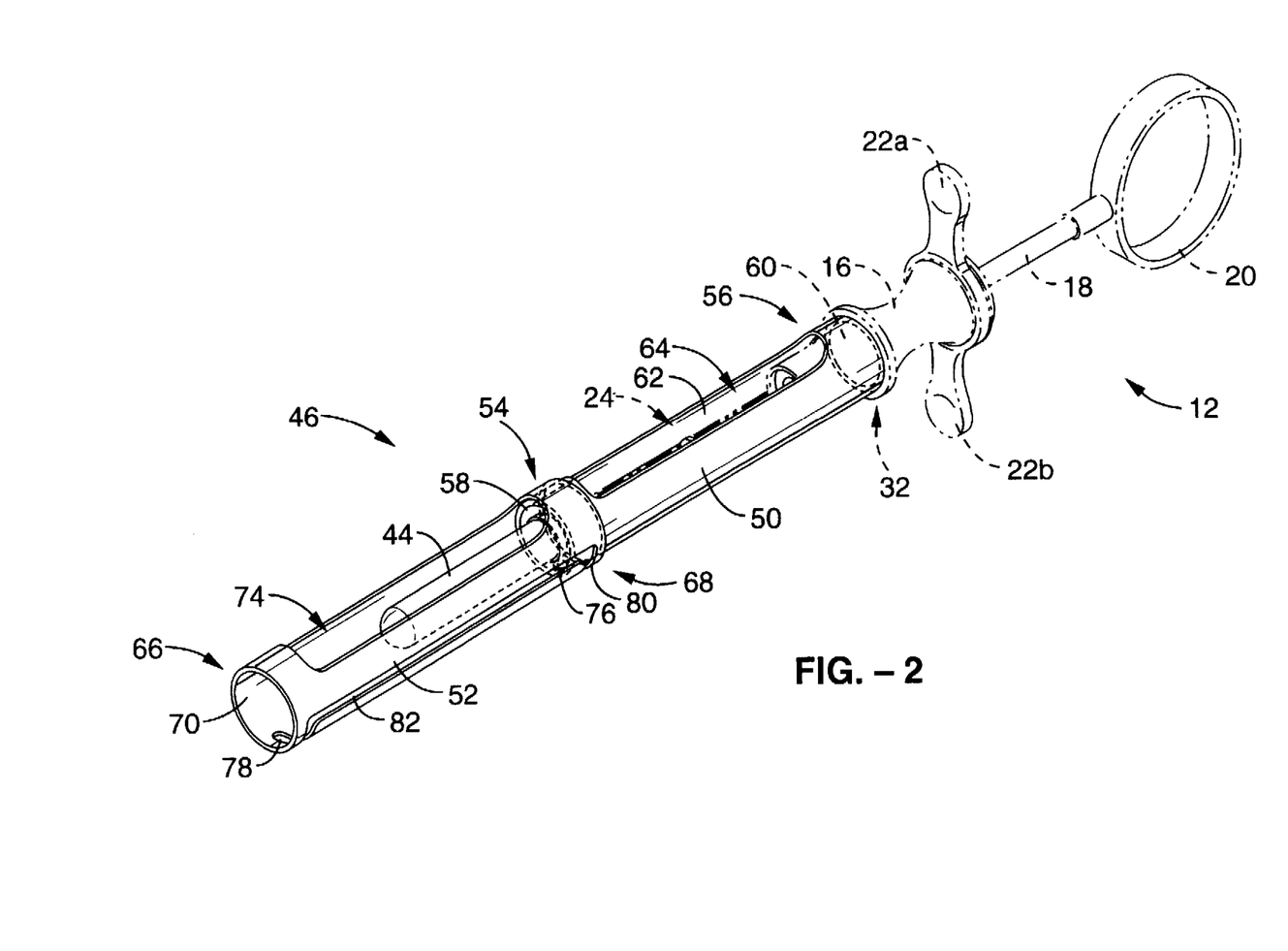
FIG. 2 is a perspective view of a syringe safety sleeve sheath shown in an extended position and coupled to an aspirating syringe.
Figure 3:
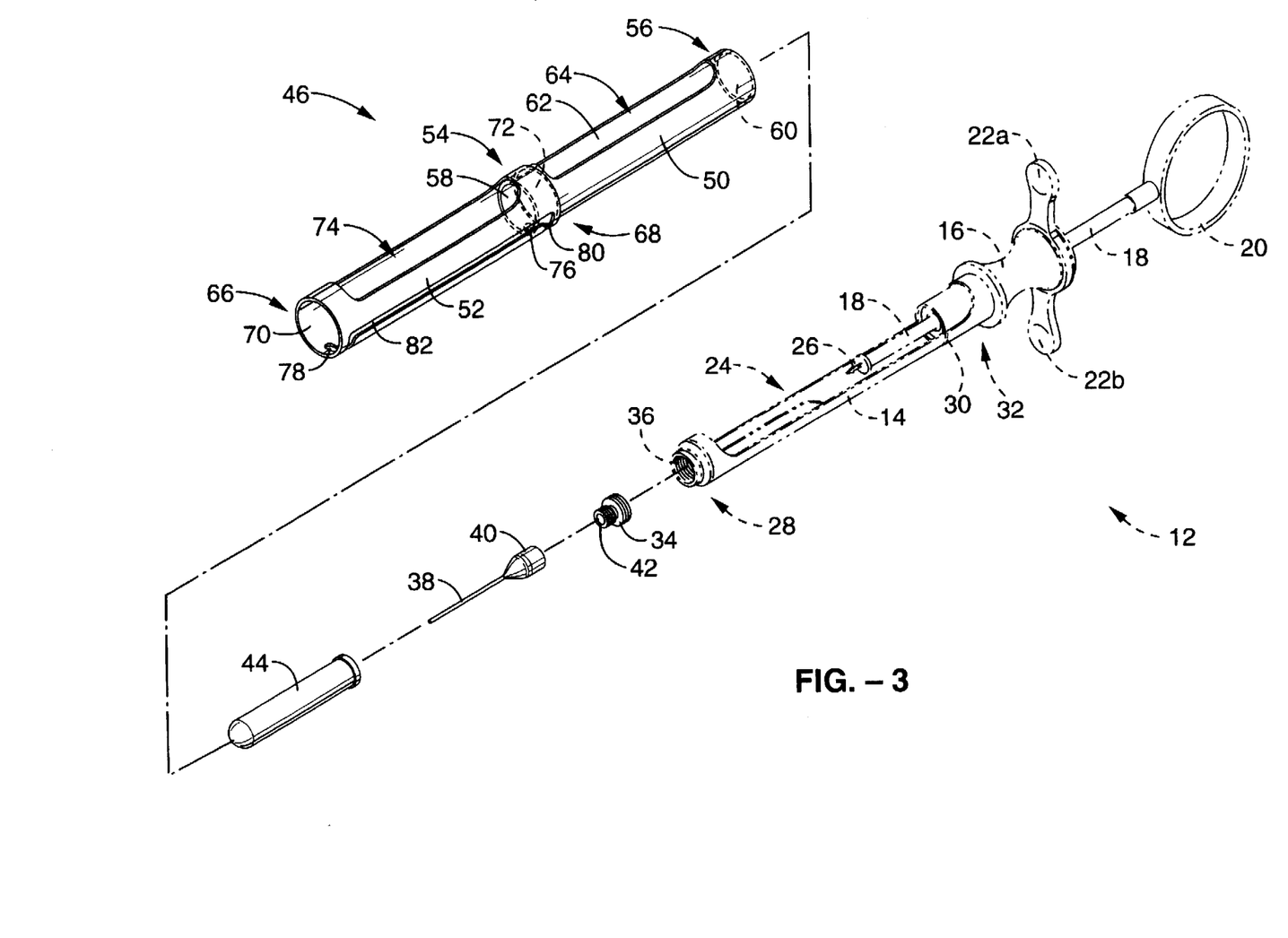
FIG. 3 is an exploded view of the assembly shown in FIG. 1.
Figure 4:
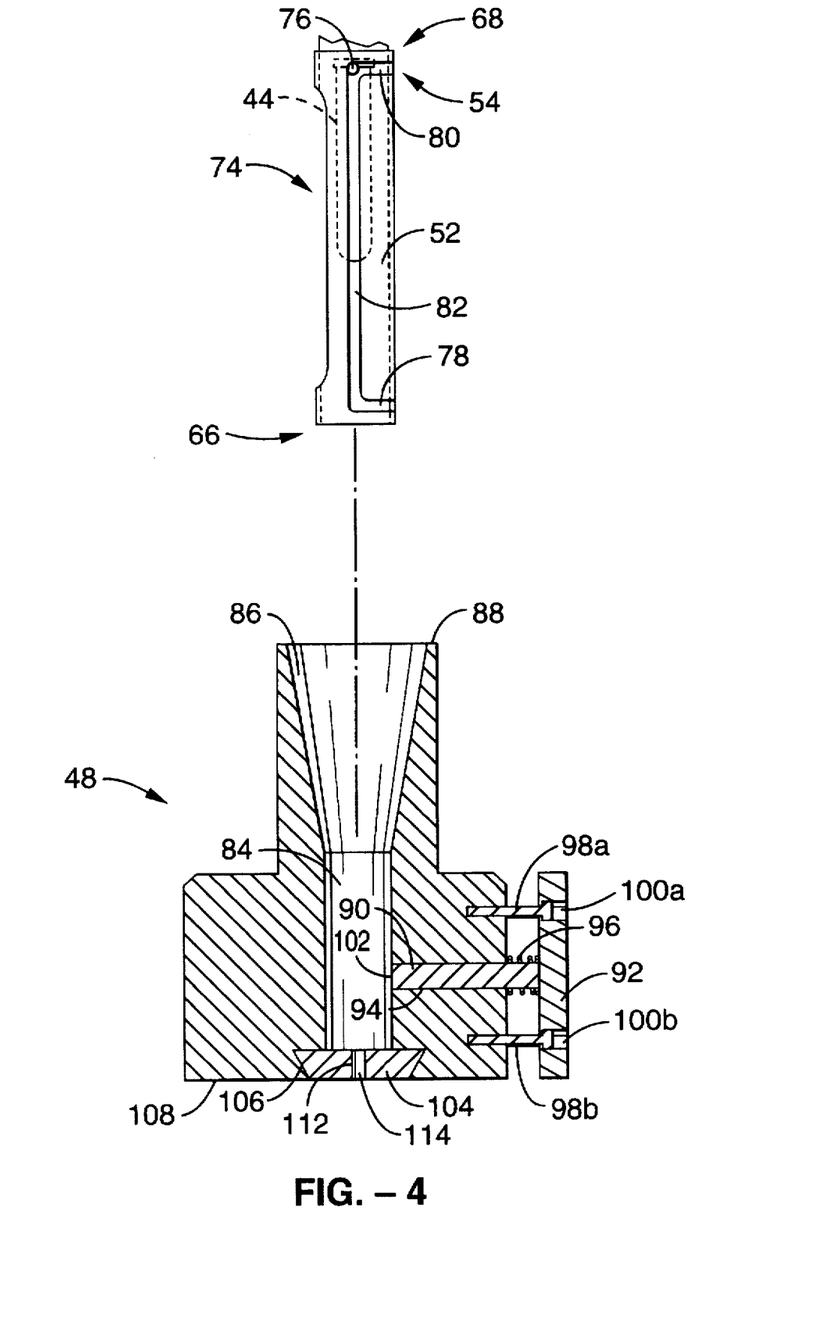
FIG. 4 is a side elevation view in cross-section showing generally the outer sleeve of a syringe safety sleeve sheath aligned with the tapered opening of a docking base.

Outer sleeve 52 reversibly slides longitudinally on inner barrel 50 between an extended, needle-protecting position, as shown in FIG. 1, FIG. 2 and FIG. 4, and a retracted position, shown in FIG. 3 and FIG. 5 through FIG. 8. In the retracted position, outer sleeve 52 generally covers or overlaps inner barrel 50, with first end 54 of inner barrel 50 generally adjacent to first end 66 of outer sleeve 52, and second end 56 of inner barrel 50 adjacent to second end 68 of outer sleeve 52. In the extended position, first end 54 of inner barrel 50 is generally adjacent second end 68 of outer sleeve 52, such that inner barrel 50 and outer sleeve 52 define an elongated hollow cylinder. While in the extended position, outer sleeve 52 encases and protects needles attached to syringe device 12, as discussed in detail below.

Figure 5:
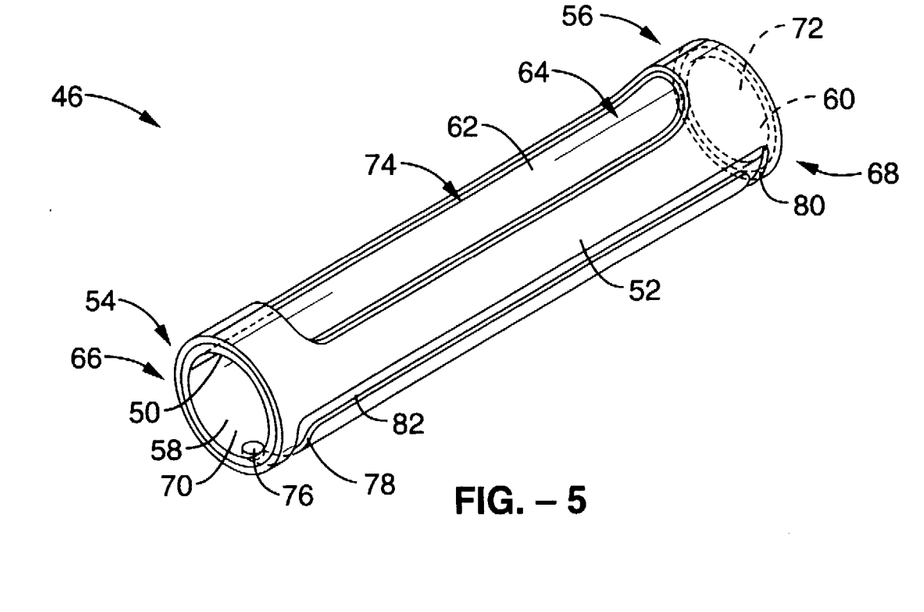
FIG. 5 is a perspective view of a syringe safety sleeve sheath in an open position while retracted.
Figure 6:
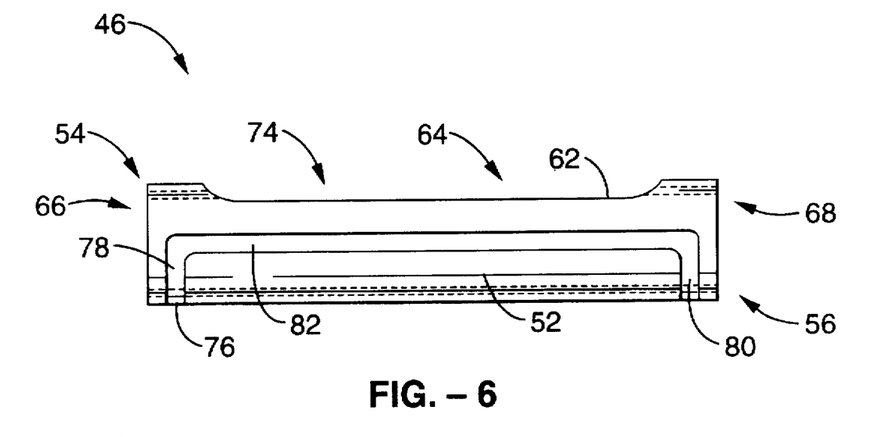
FIG. 6 is a side elevation view of the syringe safety sleeve of FIG. 5.
Figure 7:
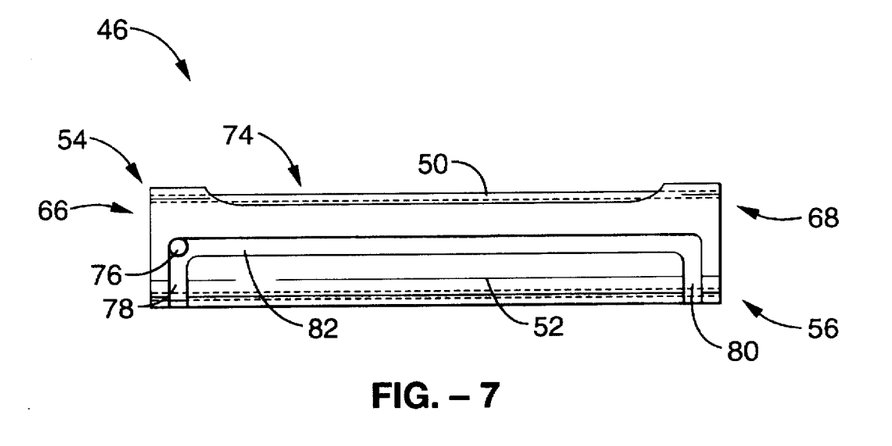
FIG. 7 is a side elevation view of a syringe safety sleeve sheath in a closed position while retracted.
Figure 8:
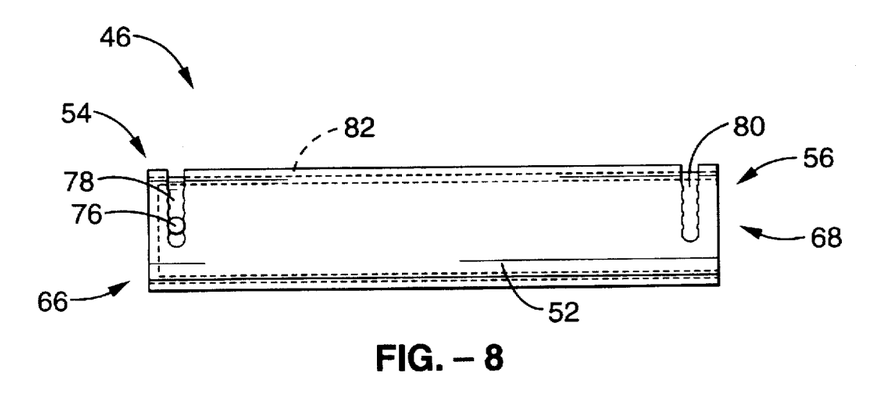
FIG. 8 is a bottom view of the syringe safety sleeve sheath of FIG. 5 and FIG. 6.

While in the retracted position, outer sleeve 52 slidably rotates or moves laterally about inner barrel 50 between an open position, shown in FIG. 5 and FIG. 6, and a closed position as shown in FIG. 7. In the open position, opening 64 in inner barrel 50 is adjacent to or aligned with opening 74 in outer sleeve, so that opening 74 communicates with bore 62 in inner barrel 50 via opening 64 in inner barrel 50. In the closed position, opening 74 in outer sleeve 52 is laterally displaced from opening 64 in inner barrel 50 such that there is no side or lateral access to bore 62 in inner barrel 50 via opening 74.

Means are provided with the invention for reversibly locking outer sleeve 52 in the retracted or extended positions relative to inner barrel 50. Preferably, the lock means comprises a stud 76 on inner barrel 50, a pair of lateral slots 78, 80 on outer sleeve 52, and a longitudinal slot 82 on outer sleeve 52 which is connected with or in communication with lateral slots 78, 80. Preferably, first lateral slot 78 is located adjacent first end 66 of outer sleeve 52, and second lateral slot 80 is located generally adjacent to second end 68 of outer sleeve 52. Lateral slots 78, 80 and longitudinal slot 82 are structured and configured to slidably receive stud 76. During the extension or retraction of outer sleeve 52 by longitudinal sliding along inner barrel 50, stud 76 slides within longitudinal slot 82 while traveling between first and second lateral slots 78, 80. When outer sleeve 52 has been slid to the extended or retracted position, outer sleeve 52 is slidably rotated on inner barrel 50 in order to move stud 76 into lateral slot 78 or lateral slot 80. While outer sleeve 52 is extended relative to inner barrel 50 and stud 76 is positioned within first lateral slot 78, stud 76 prevents outer sleeve 52 from being slidably retracted over inner barrel 50. Similarly, while outer sleeve 52 is in the retracted position on inner barrel 50 and stud 76 is positioned within second lateral slot 80, stud 76 prevents outer sleeve 52 from being slidably extended relative to inner barrel 50. Preferably, a plurality of serrations 84 (FIG. 8) are included along the edges of first lateral slot 78 to aid in retaining stud 76 within lateral slot 78 by means of reversible snap fitting over serrations 84. Likewise, a plurality of serrations 86 are provided with second lateral slot 80 to aid in the retention of stud 76 therein. Serrations 84, 86 help retain stud 76 within lateral slots 78, 80 respectively and prevent stud 76 from inadvertently disengaging from lateral slots 78, 80 during use, as described further below.

The reversible lock means of the invention also serves as means for retaining outer sleeve 52 on inner barrel 50, without which outer sleeve 52 may disengage or become separated from inner barrel 50. Other reversible lock means and/or retention means are also contemplated for use with the invention. For example, various snap-fitting structural features such as resilient ribs or resilient studs and slots may be used in association with the inner surface of outer sleeve 52 and outer surface of inner barrel 50 which can reversibly hold outer sleeve 52 in the extended and retracted positions, and prevent outer sleeve 52 from sliding entirely off inner barrel 50.

The sheath 46 of the syringe safety sleeve adapter apparatus 10 includes means for detachably coupling inner barrel 52 to syringe barrel 14 of syringe device 12. Preferably, the detachable coupling means comprises a frictional interaction between hip 30 of syringe barrel 14 on syringe device 12 and the inner surface of inner barrel 52 along longitudinal bore 62, when syringe barrel 14 is slidably engaged within bore 62. Thus, when syringe barrel 14 is inserted within bore 62 of inner barrel 50, and second end 56 of inner barrel is positioned adjacent base 16 of syringe device 12, hip 30 frictionally engages inner barrel 50 and retains inner barrel 50 of sheath 46 on the syringe device 12. The dimensions, structure, and configuration of inner barrel 50, outer sleeve 52, and bore 62 in inner barrel 50 may be varied as required to accommodate differing types, structures and configurations of syringe devices with which the invention is used.

Referring now more particularly to FIG. 3, FIG. 4, FIG. 9 and FIG. 10, the docking base 48 of the syringe safety sleeve adapter apparatus 10 includes an internal, needle receiving bore 84 which preferably is oriented vertically within docking base 48. Bore 84 is structured and configured to receive a needle 38 encased in cover 44, as described below. A tapered opening 86 in the top 88 of docking base 48 communicates with bore 84, with opening 86 being structured and configured to reversibly receive first end 66 of outer sleeve 52.

Figure 9:
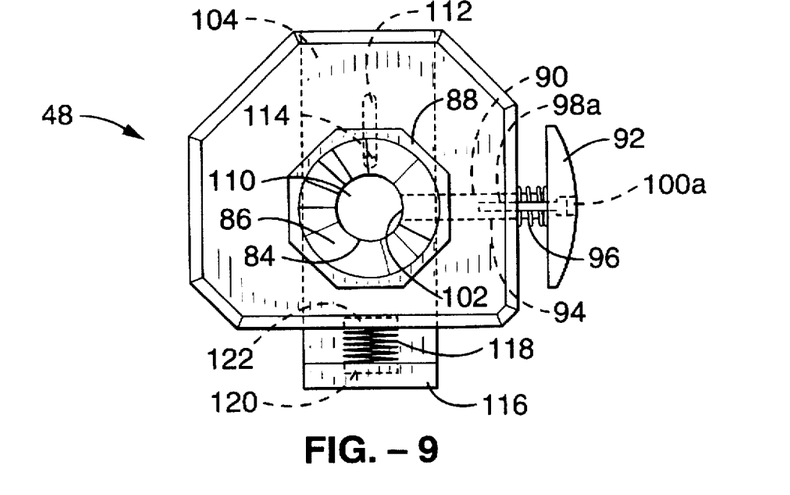
FIG. 9 is a top plan view of a docking base showing a bottom door in an open position
Figure 10:
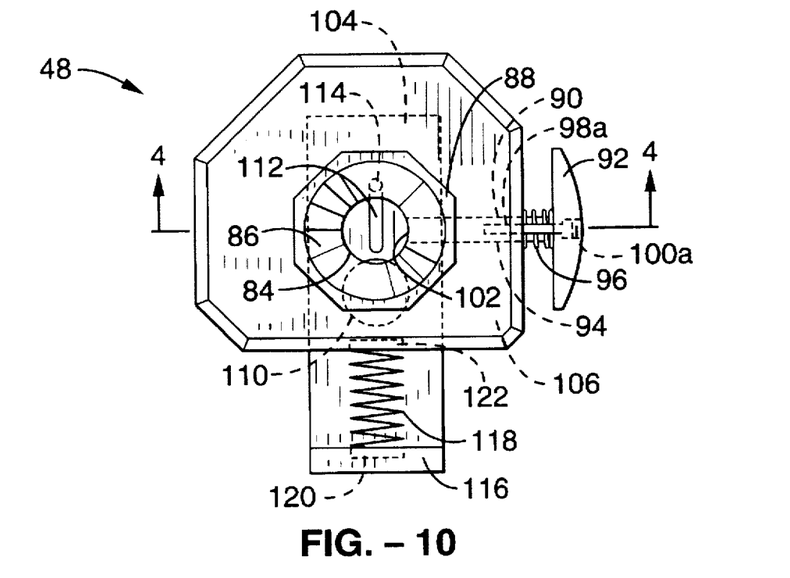
FIG. 10 is a top plan view of the docking base of FIG. 8 with the bottom door in a closed position.

Means for reversibly engaging and holding a needle cover 44 within bore 84 are included with docking base 48, and preferably comprise a spring loaded rod 90 coupled to a button 92. Rod 90 communicates with bore 84 from the side of docking base 48 via opening 94 in docking base 48, and spring 96 provides bias to rod 90 in a standard fashion. Guide pins 98a, 98b on base are slidably accommodated by channels 100a, 100b respectively in button 92. The inner end 102 of rod 90 is structured and configured to engage and hold a needle cover 44 within bore 84 when rod 90 is actuated by button 92, as discussed further below.

Exit means for removing used needles 38 from bore 84 are preferably included with docking base, and preferably comprise a door 104 which is slidably mounted within a slot 106 in the bottom 108 of docking base 48. Door 104 slides between a first, open position, shown in FIG. 9, and a second, closed position shown in FIG. 10. In the open position, an aperture 110 in door 104 is aligned with bore 84 so that needle 38 with cover 44 may exit bore 84 through the bottom 108 of docking base 48. In the closed position, door 104 is slidably moved within slot 106 so that aperture 110 is not aligned with bore 84. Preferably, a channel 112 (FIG. 10) is included in door 104, and a pin 114 provided in slot 106, with pin 114 slidably accommodated by channel 112. Pin 114 prevents door 104 from disengaging from slot 106 and becoming separated from docking base 48.

A tab or pushing member 116 is included on door 104 and extends upward therefrom at generally a right angle, to facilitate opening and closing of door 104 by a user. Preferably, bias means in the form of spring 118 are provided to retain door 104 in the closed position and prevent inadvertent loss of needles from bore 84. One end of spring 118 is attached to tab 116 in an opening 120 in tab, and the other end of spring 118 is attached to base 48 in opening 122. Spring 118 is in a relaxed position while door 104 is the closed position shown in FIG. 10. When a user pushes on tab 116 to move door 104 to the open position wherein aperture 110 in door 104 is aligned with bore 84, spring 118 is compressed, as shown in FIG. 9.

The syringe safety sleeve apparatus 10 comprising the present invention is generally used by coupling sheath 46 onto syringe device 12 by means of slidably engaging syringe barrel 14 into bore 62 of inner barrel 50 of sheath 46. As described above, hip 30 on syringe barrel 14 frictionally engages inner barrel 50 along bore 62 adjacent second end 56 of inner barrel, thereby detachably coupling sheath 46 to syringe device 12. Needle adapter 34 is preferably threaded into bore 36 prior to attachment of sheath 46 to syringe device 12. An ampule (not shown) may be inserted into syringe barrel 14 via opening 24 prior to sliding inner barrel 52 over syringe barrel 14. Alternatively, after inner barrel 50 is coupled to syringe device 12, opening 64 in inner barrel 50 can be aligned with opening 24 in syringe barrel 14, and an ampule then placed in syringe barrel 14 while outer sleeve is extended. Or, alternatively, while outer sleeve 52 is in the retracted position on inner barrel 50, outer sleeve 52 may be rotated relative to inner barrel 50 to the open position described above so that opening 74 in outer sleeve is adjacent opening 64 in inner barrel, and an ampule may be placed within syringe barrel 14. While outer sleeve is in the retracted position, a needle 38 with attached cover 44 is attached to syringe device 12 by threadably engaging needle base 40 onto ferrule 42 in a conventional manner. Since cover 44 has not yet been removed from needle 38, there is generally no danger of needle puncture yet to persons using syringe device 12 with the invention.

After needle 38 is attached to syringe device and prior to removal of cover 44 from needle 38, with outer sleeve 52 in the retracted position, needle 38 and cover 44 are inserted into bore 84 of docking base 48 with door 104 in the closed position described above, until cover 44 contacts door 104 at the bottom 108 of docking base 48. First end 66 of outer sleeve 52 is accommodated by tapered opening 86 in the top 88 of docking base 48 as needle 38 and cover 44 are received by bore 84. When needle 38 and cover 44 are thus positioned within bore 84, button 92 is pushed to slide rod 90 through opening 94 until end 102 of rod 90 contacts cover 44 of needle 38. Guide pins 98a, 98b on base 48 slide through channels 100a, 100b in button 92 as button 92 is actuated. As mentioned above, cover 44 is held onto needle 38 by frictionally engaging needle base 40. While pressure is applied to button 92 to hold rod end 102 against needle cover 44, the syringe device 12 is pulled upward by the user of the invention to disengage cover 44 from needle 38, with rod end 102 holding the needle cover 44 fixedly within bore 84. Once cover 44 has become disengaged from needle 38, button 92 is released, and spring 96 retracts rod 90 as spring 96 returns to its resting position. Cover 44 remains within bore 84 adjacent door 104 in the bottom 108 of docking base 48. As the now uncovered needle 38 is drawn out of bore 84 by upward motion of the attached syringe device 12, the user of the invention slidably extends outer sleeve 52 from the retracted position to the extended position in the manner described above while first end 66 of outer sleeve 52 is held within opening 86 at the top 88 of docking base 48.

Thus, the uncovered needle 38 attached to syringe device 12 is isolated from persons using the invention during the removal of cover 44, which occurs while needle 38 is within bore 84 of docking base 48, and during the withdrawal of needle 38 from bore 84, since outer sleeve 52 is extended as needle 38 is withdrawn from bore 84 and docking base 48. Prior to needle 38 clearing opening 86 in the top 88 of docking base 48, outer sleeve 52 reaches its fully extended position, encasing or sheathing the needle 38 within outer sleeve 52 so that persons using the invention are not exposed to uncovered needle 38. Outer sleeve 52 may be locked into the extended position, as described above, by sliding stud 76 into lateral slot 78, thereby preventing unwanted retraction of outer sleeve 52 during handling of syringe device 12. When syringe device 12 is in position to deliver anesthetic or other drug by injection via needle 38, or to obtain a body fluid sample, stud 76 is disengaged from lateral slot 78, and outer sleeve 52 is slidably retracted onto inner barrel 50 as described above, so that needle 38 is exposed through opening 70 in first end 66 of outer sleeve 52. If desired, first end 66 of outer sleeve 52 may be placed in contact with the area of injection prior to retraction of outer sleeve 52, and the user of the invention may view needle 38 during injection through opening 74 in outer sleeve 52 as outer sleeve 52 is retracted.

Following injection, as needle 38 is removed from the injection recipient, outer sleeve 52 is again slidably extended, and stud 76 is locked into lateral slot 78 to lock outer sleeve 52 in the extended position to enclose or house the now contaminated needle 38. To remove and dispose of the contaminated needle 38 on syringe device 12, the user of the invention inserts first end 66 of outer sleeve 52 into opening 86 in docking base 48, and unlocks stud 76 from lateral slot 78 so that outer sleeve 52 may be slidably retracted on inner barrel 50 while first end 66 of outer sleeve 52 is positioned within opening 86. As outer sleeve 52 is retracted, the contaminated needle 38 enters bore 84 of docking base 48 and is re-inserted into cover 44, which was left within bore 84 after the initial removal of cover 44 from needle 38 described above. Cover 44 engages base 40 of needle 38 by friction, and is again held onto needle 38. The user of the invention then presses button 92 to move end 102 of rod 90 against cover 44 to hold cover in place, and syringe device 12 is rotated to unthread needle base 40 from ferrule 42, leaving the contaminated needle 38, encased by cover 44, within bore 84 of docking base 48. The user of the invention then places docking base 48 over a contaminated needle receptacle (not shown), and pushes tab 116 to slide door 104 in the bottom 108 of docking base 48 to the open position, described above, wherein aperture 110 is aligned with bore 84, allowing needle 38 and attached cover 44 to exit docking base 48 via aperture 110 for disposal in the receptacle. When the user stops pushing or releases tab 116, spring 126 automatically moves door 104 back to the closed position.

As can be seen from the above, the syringe safety sleeve apparatus 10 provides for protection from exposed syringe needles at every stage of use, including during attachment and removal of needles from syringe device 12, during removal and replacement of needle cover 44 on needle 38, during all stages of use when needle 38 is not within bore 48 of docking base 48, and during disposal of the used needle. Since cover 44 is removed from and replaced on needle 38 while needle 38 is within bore 84 of docking base, persons using the invention avoid inadvertent needle puncture wounds associated with removal and replacement of cover 44. Since outer sleeve 52 is placed in the extended position after needle 38 is removed from bore 84 of docking base and is locked in the extended position except during injection, the user of the invention avoids contact with the needle during handling of syringe device 12. The needle cover holding means and exit means associated with docking base 48 allow the contaminated needle to be removed from syringe device 12 and placed into a receptacle without exposure of the needle to persons using the invention.

Preferably, inner barrel 50 and outer sleeve 52 of sheath 46, as well as docking base 48 and its components, are made of durable metallic and/or polymeric material which can be sterilized by autoclaving and re-used. Alternatively, inner barrel 50 and outer sleeve 52 may be made from inexpensive material and sheath 46 then disposed of after use.

Figure 11:
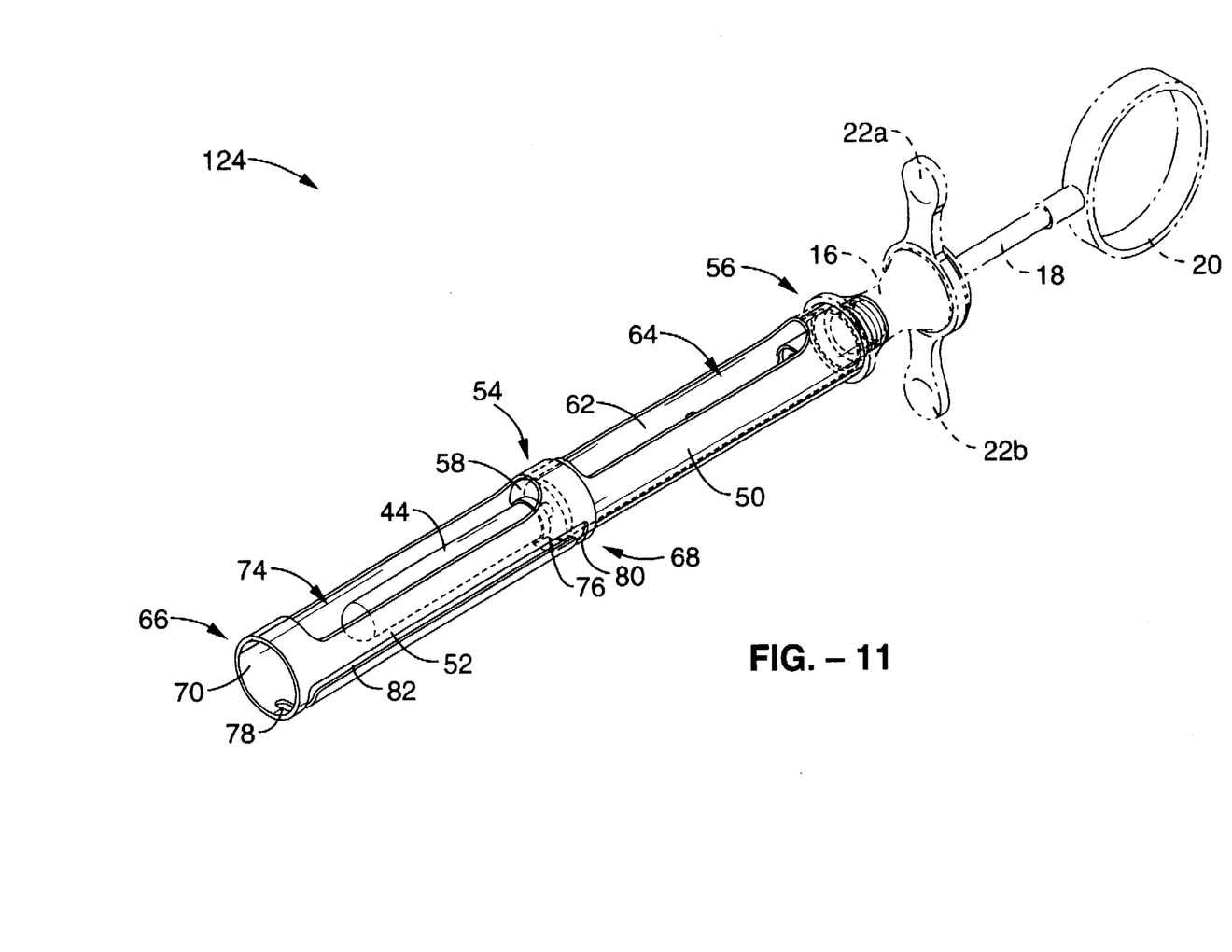
FIG. 11 is a perspective view of an alternative embodiment syringe safety sleeve sheath shown in an extended position and coupled to an aspirating syringe.
Figure 12:
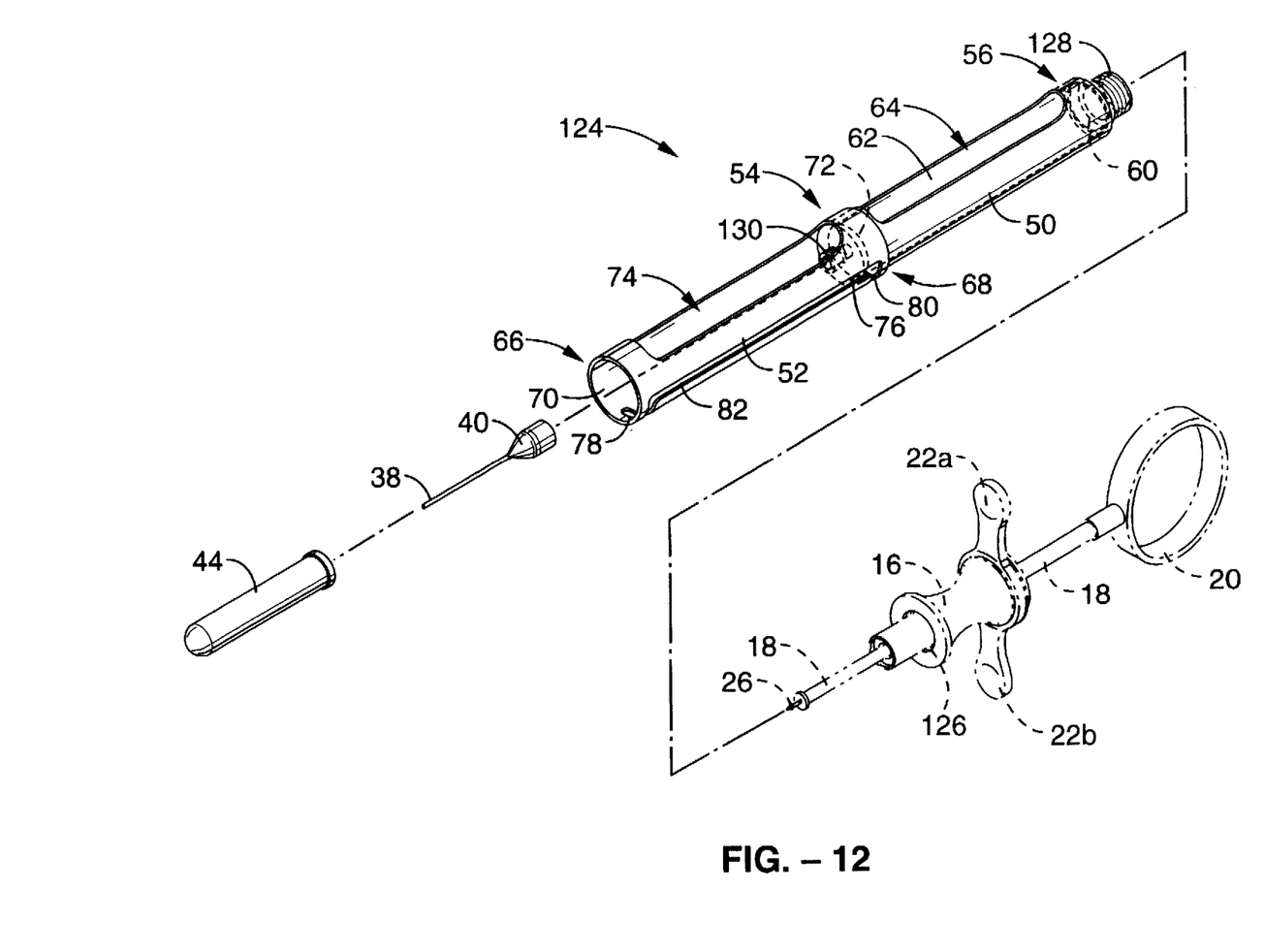
FIG. 12 is an exploded view of the assembly shown in FIG. 11.
Figure 13:
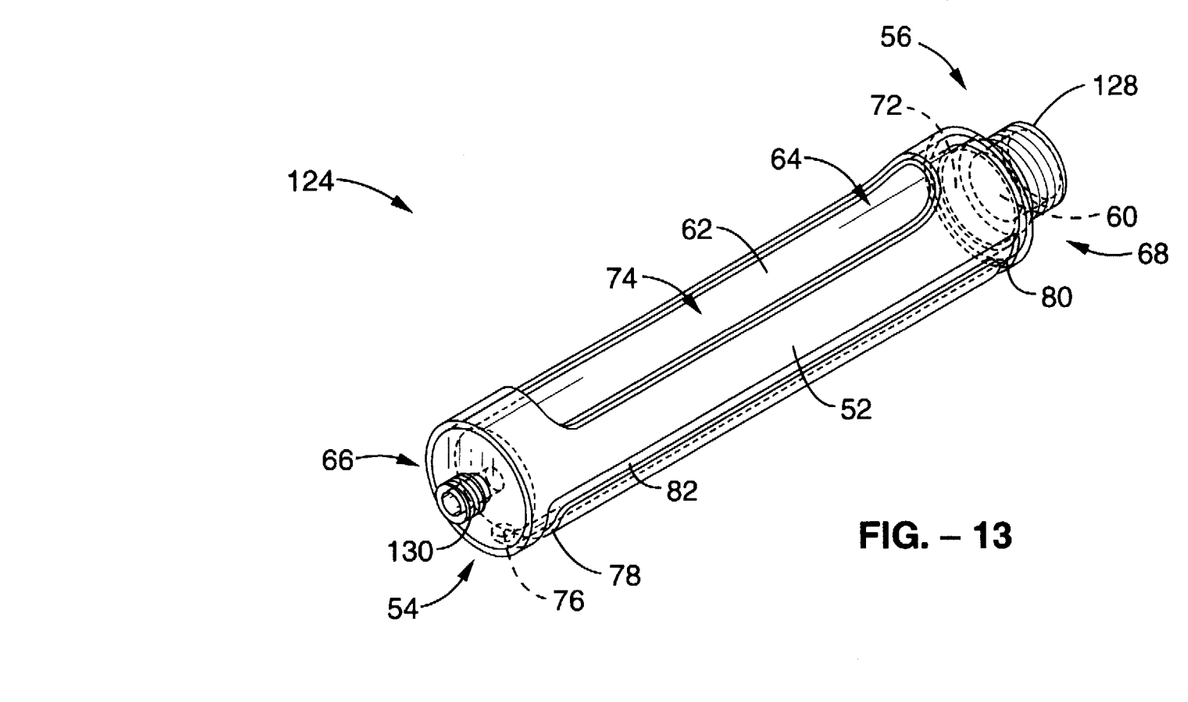
FIG. 13 is a perspective view of the syringe safety sleeve sheath of FIG. 11 and FIG. 12 shown retracted and in an open position.

Referring now to FIG. 11 through FIG. 13, an alternative embodiment of a sheath 124 in accordance with the present invention is generally shown, wherein like reference numerals denote like parts. As mentioned above, syringe barrel 14 is detachably coupled to the base 16 of syringe device, and may be unthreaded from base to expose an internally threaded opening 126 on base 16. As with the embodiment described above, sheath 124 includes an outer sleeve 52 which is slidably disposed on an inner barrel 50, with inner barrel 50 including an opening 60 at second end 56, and outer sleeve including openings 70, 72 at first and second ends. Side-facing openings 64, 74 in inner barrel 50 and outer sleeve 52 respectively provide access to bore 62 within inner barrel 50. The means for detachably coupling inner barrel 50 to syringe device 12 comprises a threaded portion 128 adjacent second end 56 of inner barrel 50, with opening 60 extending through threaded portion 128. First end 54 of inner barrel 50 is closed, and includes a threaded ferrule 130 structured and configured to attach to needle base 40.

The sheath 124 operates in a manner substantially the same as that described above for sheath 46, with the primary exception being that sheath 124 is designed for use with syringe device 12 where syringe barrel 14 has been removed therefrom. Inner barrel 50 of sheath 124 is coupled to base 16 by engaging threaded portion 128 on second end 56 of inner barrel 50. Syringe needles are threaded onto ferrule 130 on first end 54 of inner barrel instead of onto the needle adapter 34 described with the above embodiment, since the syringe barrel 14 and attached needle adapter 34 are not required when sheath 124 is used. Inner barrel 50 thus provides the same functions provided by syringe barrel 14.

Other means for detachably coupling inner barrel 50 to syringe device 12 are also contemplated for use with the present invention, including various threading arrangements and reversible snap fitting features associated with inner barrel 50. It is further contemplated that inner barrel 50 could be an integral to base 16 of syringe device 12 and permanently attached thereto. However, in order to facilitate sterilization of the slidably related inner barrel 50 and outer sleeve 52 of the invention for re-use, inner barrel 50 preferably is detachably coupled to syringe device 12.

Figure 14:
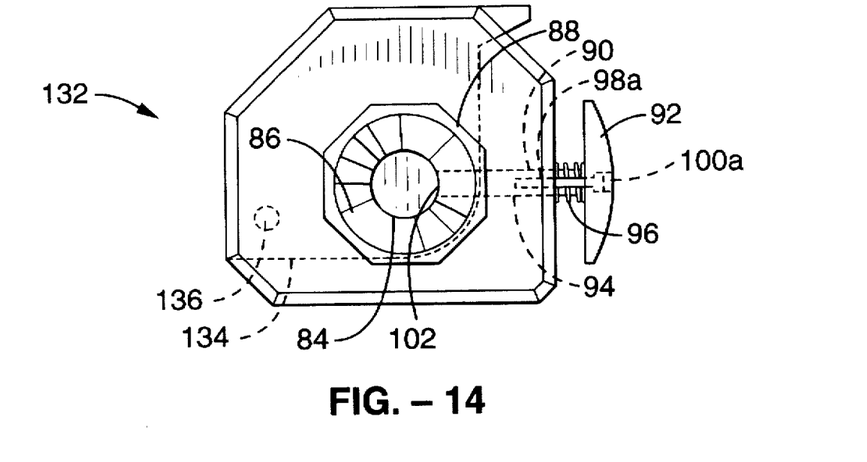
FIG. 14 is a top plan view of an alternative embodiment of a docking base in accordance with the present invention, shown with a bottom door in a closed position.
Figure 15:
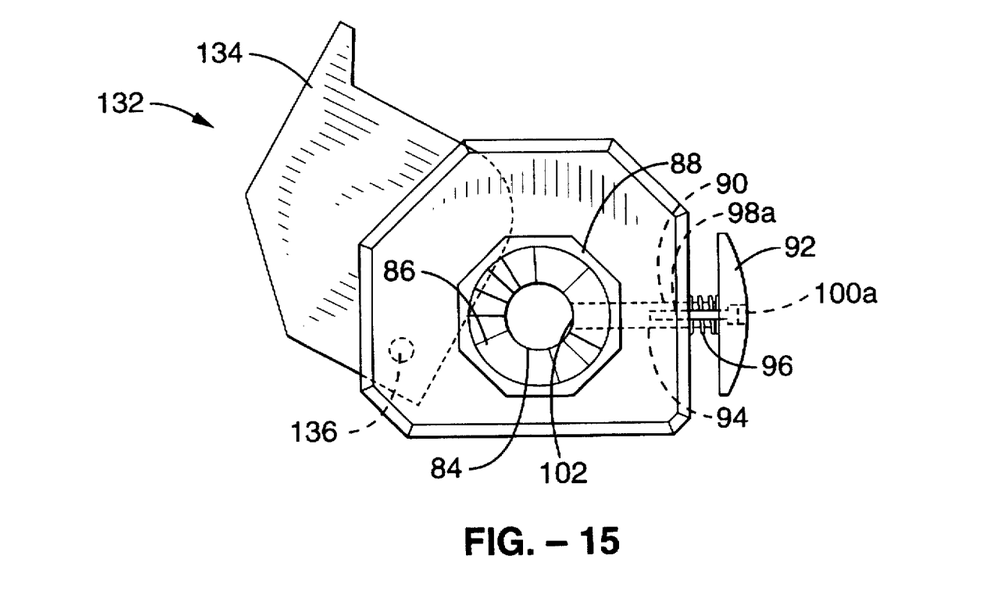
FIG. 15 is a top plan view of the docking base of FIG. 15 shown with the bottom door in an open position.

Referring now to FIG. 14 and FIG. 15, an alternative embodiment of a docking base 132 in accordance with the present invention is generally shown. Docking base 132 includes a pivoting door 134 which moves pivotally about pin 136 to allow used needles to exit bore 84 in docking base into a disposal receptacle. In all other respects, docking base 132 is used in generally the same manner as described above for docking base 48.

Accordingly, it will be seen that this invention provides a syringe safety sleeve apparatus which protects users inadvertent syringe needle puncture wounds at each stage of use, including attachment and removal of needles from the syringe device, removing and replacing needle covers on needles, during injection with the syringe device, and during disposal of the used needles. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A syringe safety sleeve adapter apparatus, comprising:
   (a) an inner barrel;
   (b) an outer sleeve, said outer sleeve slidable disposed on said inner barrel;
   (c) means for reversibly locking said sleeve in an extended position on said barrel;
   (d) wherein said outer sleeve slidably moves on said inner barrel between a retracted position and said extended position;
   (e) a side-facing opening in said inner barrel and a side-facing opening in said outer sleeve; and
   (f) means for coupling said barrel to a syringe device.

2. A syringe safety sleeve adapter apparatus as recited in claim 1, wherein, when said outer sleeve is in said retracted position, said outer sleeve reversibly and slidably rotates on said barrel between an open position wherein said opening in said inner barrel is adjacent said opening in said outer sleeve, and a closed position wherein said opening in said outer sleeve is laterally displaced relative to said opening in said inner barrel.

3. A syringe safety sleeve adapter apparatus as recited in claim 2, wherein said reversibly locking means comprises a stud on said inner barrel and a lateral slot and a longitudinal slot on said outer sleeve, said lateral slot connected to said longitudinal slot, said lateral and longitudinal slots slidably receiving said stud.

4. A syringe safety sleeve adapter apparatus as recited in claim 3, wherein said inner barrel includes a first end and a second end, and outer sleeve includes a first end and a second end, said first and second ends of said outer sleeve each including an opening, said stud positioned adjacent said first end of said inner barrel, said lateral slot positioned adjacent said first end of said outer sleeve.

5. A syringe safety sleeve adapter apparatus, comprising:
   (a) a hollow, cylindrical inner barrel, said inner barrel including a side-facing opening;
   (b) a hollow, cylindrical outer sleeve, said outer sleeve slidably disposed on said inner barrel, said outer sleeve including a side-facing opening, said outer sleeve reversibly sliding longitudinally on said inner barrel between an extended position and a retracted position;
   (c) a stud on said inner barrel, and a lateral slot and a longitudinal slot on said outer sleeve, said lateral slot connected to said longitudinal slot, said lateral and longitudinal slots slidably receiving said stud; and (d) means for coupling said barrel to a syringe device.

6. A syringe safety sleeve adapter apparatus as recited in claim 5, wherein, when said outer sleeve is in said retracted position, said outer sleeve reversibly and slidably rotates on said barrel between an open position wherein said opening in said inner barrel is adjacent said opening in said outer sleeve, and a closed position wherein said opening in said outer sleeve is laterally displaced relative to said opening in said inner barrel.

7. A syringe safety sleeve adapter apparatus as recited in claim 5, wherein said inner barrel includes a first end and a second end, and outer sleeve includes a first end and a second end, said first and second ends of said outer sleeve each including an opening, said stud positioned adjacent said first end of said inner barrel, said lateral slot positioned adjacent said first end of said outer sleeve.

8. A syringe safety sleeve adapter and docking apparatus, comprising:
   (a) a hollow, cylindrical inner barrel, said inner barrel including a side-facing opening, said inner barrel including first and second ends;
   (b) a hollow, cylindrical outer sleeve, said outer sleeve slidably disposed on said inner barrel, said outer sleeve including a side-facing opening, said outer sleeve including first and second ends, said outer sleeve reversibly sliding longitudinally on said inner barrel between an extended position and a retracted position;
   (c) means for reversibly locking said sleeve on said barrel in said extended position and said retracted position;
   (d) means for coupling said inner barrel to a syringe device; and
   (e) a docking base, said docking base including a needle receiving bore, said docking base having an opening communicating with said bore, said opening structured and configured to reversibly and detachably receive said outer sleeve.

9. An apparatus as recited in claim 8, wherein said docking base further comprises:
   (a) means for reversibly holding a needle cover within said bore; and
   (b) exit means for removing used needles from said bore.

10. An apparatus as recited in claim 8, wherein, when in said retracted position, said outer sleeve reversibly and slidably rotates on said inner barrel between an open position wherein said opening in said inner barrel is adjacent said opening in said outer sleeve, and a closed position wherein said opening in said outer sleeve is laterally displaced relative to said opening in said inner barrel.

11. An apparatus as recited in claim 8, wherein said reversible lock means comprises:
   (a) a stud, said stud located included on said inner barrel adjacent said first end;
   (b) a first lateral slot, said first lateral slot included on said outer sleeve adjacent said first end, said first lateral slot slidably receiving said stud;

(c) a second lateral slot, said second lateral slot included on said outer sleeve adjacent said second end, said second lateral slot slidably receiving said stud; and
   (d) a longitudinal slot on said outer sleeve, said longitudinal slot connected with said first and second lateral slots, said longitudinal slot slidably receiving said stud.

12. An apparatus as recited in claim 8, wherein said first and second ends of said outer sleeve each including an opening, and said first and second ends of said inner barrel each include an opening, said opening in said second end of said inner barrel structured and configured to tensionally engage a hip on a syringe barrel.

13. An apparatus as recited in claim 8, wherein said first end of said inner barrel includes means for reversibly attaching a needle, said first and second ends of said outer sleeve each including an opening, and said means for coupling said inner barrel to a syringe device is included on said second end of said inner barrel.

14. A syringe safety sleeve adapter and docking apparatus, comprising:
   (a) an inner barrel;
   (b) an outer sleeve, said outer sleeve slidably disposed on said inner barrel;
   (c) means for reversibly locking said sleeve in an extended position on said barrel;
   (d) means for coupling said barrel to a syringe device; and
   (e) a docking base, said docking base including a needle receiving bore, said docking base having an opening communicating with said bore, said opening structured and configured to reversibly and detachably receive said outer sleeve, said docking base including means for reversibly holding a needle cover within said bore.

15. An apparatus as recited in claim 14, wherein said docking base includes exit means for removing used needles from said bore.

16. A syringe safety sleeve adapter and docking apparatus, comprising:
   (a) a hollow, cylindrical inner barrel, said inner barrel including a side-facing opening;
   (b) a hollow, cylindrical outer sleeve, said outer sleeve slidably disposed on said inner barrel, said outer sleeve including a side-facing opening, said outer sleeve reversibly sliding longitudinally on said inner barrel between an extended position and a retracted position;
   (c) means for reversibly locking said sleeve in said extended position on said barrel;
   (d) means for coupling said barrel to a syringe device; and
   (e) a docking base, said docking base including a needle receiving bore, said docking base having an opening communicating with said bore, said opening structured and configured to reversibly and detachably receive said outer sleeve, said docking base including means for reversibly holding a needle cover within said bore.

17. An apparatus as recited in claim 16, wherein said docking base includes exit means for removing used needles from said bore.

* * * * *